US00PP11930P2

(12) United States Plant Patent
Booman

(10) Patent No.: US PP11,930 P2
(45) Date of Patent: Jun. 19, 2001

(54) BEGONIA PLANT NAMED 'MIAMI STORM'

(76) Inventor: James Lawrence Booman, 2302 Bautista Ave., Vista, CA (US) 92084

( * ) Notice: Subject to any disclaimer, the term of this patent is extended or adjusted under 35 U.S.C. 154(b) by 0 days.

(21) Appl. No.: 09/375,778

(22) Filed: Aug. 17, 1999

(51) Int. Cl.[7] ..... A01H 5/00
(52) U.S. Cl. ..... Plt./343

(58) Field of Search ..... Plt./343

*Primary Examiner*—Bruce R. Campell
*Assistant Examiner*—Anne Marie Grünberg
(74) *Attorney, Agent, or Firm*—C. A. Whealy

(57) ABSTRACT

A new and distinct cultivar of Rex Begonia plant named 'Miami Storm', characterized by its uniform growth habit; moderate plant vigor; no requirement for winter dormancy; and interesting and attractive leaf coloration and pattern.

1 Drawing Sheet

BACKGROUND OF THE INVENTION

The present invention relates to a new and distinct cultivar of Begonia plant, botanically known as *Begonia rex* hybrid, commercially known as Rex Begonia, and hereinafter referred to by the name 'Miami Storm'.

The new Rex Begonia was discovered and selected by the Inventor in a controlled environment in Vista, Calif., in 1995, within a large group of seedling progeny from multiple crossings of unidentified selections of *Begonia rex* hybrids.

The selection of this plant was based on its uniform growth habit, moderate plant vigor, and attractive foliage coloration and pattern.

Asexual reproduction of the new Rex Begonia by leaf cuttings taken in a controlled environment in Vista, Calif., has shown that the unique features of this new Rex Begonia are stable and reproduced true to type in successive generations.

SUMMARY OF THE INVENTION

The cultivar 'Miami Storm' has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Miami Storm'. These characteristics in combination distinguish 'Miami Storm' as a new and distinct Rex Begonia:

1. Uniform growth habit.
2. Moderate plant vigor.
3. Does not require winter dormancy.
4. Interesting and attractive leaf coloration and pattern.

In side-by-side comparisons conducted by the Inventor in Vista, Calif., plants of the new Rex Begonia differ from plants of the nonpatented cultivar Merry Christmas Corkscrew in the following characteristics:

1. Plants of the new Rex Begonia grow more rapidly than plants of the cultivar Merry Christmas Corkscrew.
2. Plants of the new Rex Begonia are more compact than plants of the cultivar Merry Christmas Corkscrew.

3. Leaves of plants of the new Rex Begonia are brighter in color than leaves of plants of the cultivar Merry Christmas Corkscrew.
4. Leaves of plants of the new Rex Begonia do not have a "corkscrew" formation whereas leaves of plants of the cultivar Merry Christmas Corkscrew have a "corkscrew" formation.
5. Plants of the new Rex Begonia do not require a winter dormancy period whereas plants of the cultivar Merry Christmas Corkscrew do require a winter dormancy period.

In side-by-side comparisons conducted by the Inventor in Vista, Calif., plants of the new Rex Begonia differ from plants of the nonpatented cultivar Lillium in the following characteristics:

1. Plants of the new Rex Begonia are more compact than plants of the cultivar Lillium.
2. Plants of the new Rex Begonia have flatter leaves than plants of the cultivar Lillium.
3. Leaves of plants of the new Rex Begonia are brighter in color than leaves of plants of the cultivar Lillium.
4. Plants of the new Rex Begonia do not require a winter dormancy period whereas plants of the cultivar Lillium do require a winter dormancy period.

BRIEF DESCRIPTION OF THE PHOTOGRAPH

The accompanying colored photograph illustrates the overall appearance of the new Rex Begonia, showing the colors as true as it is reasonably possible to obtain in colored reproductions of this type. The photograph comprises a top perspective view of a typical plant of 'Miami Storm'. Foliage colors in the photograph may differ from the actual colors due to light reflectance.

DETAILED BOTANICAL DESCRIPTION

In the following description, color references are made to The Royal Horticultural Society Colour Chart except where general terms of ordinary distionary significance are used. The following observations and measurements describe plants grown during the spring in Vista, Calif., under conditions which approximate commercial practice. Plants used for this description were grown in 15-cm containers for about 3 months.

Botanical classification: *Begonia rex* hybrid cultivar Miami Storm.

Commercial classification: Rex Begonia.

Parentage: Chance seedling of multiple crossings of unidentified selections of *Begonia rex* hybrids.

Propagation:

*Type.*—Leaf cuttings.

*Time to initiate roots, summer.*—About 56 days at 21° C.

*Time to initiate roots, winter.*—About 56 days at 21° C.

*Time to develop roots, summer.*—About 84 days at 21° C.

*Time to develop roots, winter.*—About 98 days at 21° C.

*Rooting habit.*—Fine, fibrous and well-branched.

Plant description:

*Plant form.*—Rosette; compact; dense and outwardly arching potted plant; freely basal branching with good leaf petiole strength.

*Vigor.*—Moderate.

*Plant height, soil surface to top of leaf canopy.*—About 23 cm.

*Plant width.*—About 57 cm.

*Leaves.*—Arrangement: Simple. Length: Petiole to apex: About 13 cm. Base to apex: About 18.2 cm. Width: About 13 cm. Shape: Asymmetrical, oblique, ovate. Apex: Acute; sometimes asymmetrically acute. Base: Asymmetrically cordate. Margin: Pectinate; irregularly sinuate. Texture: Leathery, rugose; pubescence on lower surface veins. Color: Young foliage, upper surface: Margin: Dark brown, 200A. Central venal areas: 200A. Blade: Iridescent, 185B to 185C to 185D, merging antemarginal with 138C to 186C to 186D. Young foliage, lower surface: Margin: Iridescent, 187B and 183A. Central venal areas: 187B and 183A. Background: 139D. Mature, fully expanded, foliage, upper surface: Margin: Dark brown, 200A. Central venal areas: 200A; spots of 184A. Blade: 184A and 184B; metallic flashes of 185A. Intermarginal: Occasional blotches of 191C. Veins: 187A. Mature, fully expanded, foliage, lower surface: Margin Darker than 183A. Blade: Darker than 183A. Background: Green, 193C; intervenal, 191B, and 184C. Veins: 183A to 183B; reticulate.

*Petioles.*—Length: About 15 cm. Diameter: About 5 mm. Shape: Longitudinally grooved. Texture: Pubescent. Color: 183B.

*Stipules.*—Length: About 1.7 cm. Diameter at base: About 1 cm. Shape: Subulate, deltoid. Color: 183B.

Flower description:

*Flowering habit.*—Male flowers, single with one whorl of four tepals. Female flowers, semi-double with three tepals interior to outer whorl of five tepals. Usually about three flowers per cyme. Flowers persistent.

*Natural flowering season.*—Plants will flower continuously, but typically plants flower more abundantly during the spring and summer.

*Flowers.*—Shape: Rounded; somewhat cup-shaped. Diameter: About 2.5 cm. Depth (height): About 1.4 cm. Aspect: Drooping about 60° from vertical. Fragrance: None.

*Flower buds.*—Shape: Elliptic, ovoid; bulbous with marginal lip. Length: About 9 mm. Diameter: About 7.5 mm. Color: Close to 48A.

*Tepals.*—Arrangement: Rosette. Length: About 1.5 cm. Width: About 1.1 cm. Shape: Ovate with rounded apex. Margin: Entire. Texture: Smooth, waxy; slightly velvety; iridescent. Color: When opening, upper surface: 48C and 48D. When opening, lower surface: 47D and 48C. Fully opened, upper surface: 55C. Fully opened, lower surface: 55D; 48C at center.

*Peduncles.*—Angle: About 45° from vertical. Length: About 1.5 cm. Diameter: About 2.5 mm. Strength: Firm. Texture: Smooth, waxy. Color: 166C.

*Pedicels.*—Angle: About 25° from vertical. Length: About 1.9 cm. Diameter: About 2 mm. Strength: Moderate, flexible. Texture: Smooth, waxy. Color: 45A.

*Reproductive organs.*—Male flowers: Stamen quantity: About 108; globose mass. Anther shape: Rhomboidal; lower sides curved inwardly. Anther length: About 8 mm. Anther color: 28A; underside, 22B. Pollen: Not observed. Female flowers: Pistil length: About 1.8 cm. Stigma shape: Funnel; bilobate. Stigma color: 25A; margin, 26B. Ovary: Inferior; three-winged; one large top wing, 51B, and two lower wings; both surfaces, 34A to 39A.

Disease resistance: Resistance to diseases common to Rex Begonia has not been determined.

Seed production: Seed production has not been observed.

It is claimed:

1. A new and distinct cultivar of Rex Begonia plant named 'Miami Storm', as illustrated and described.

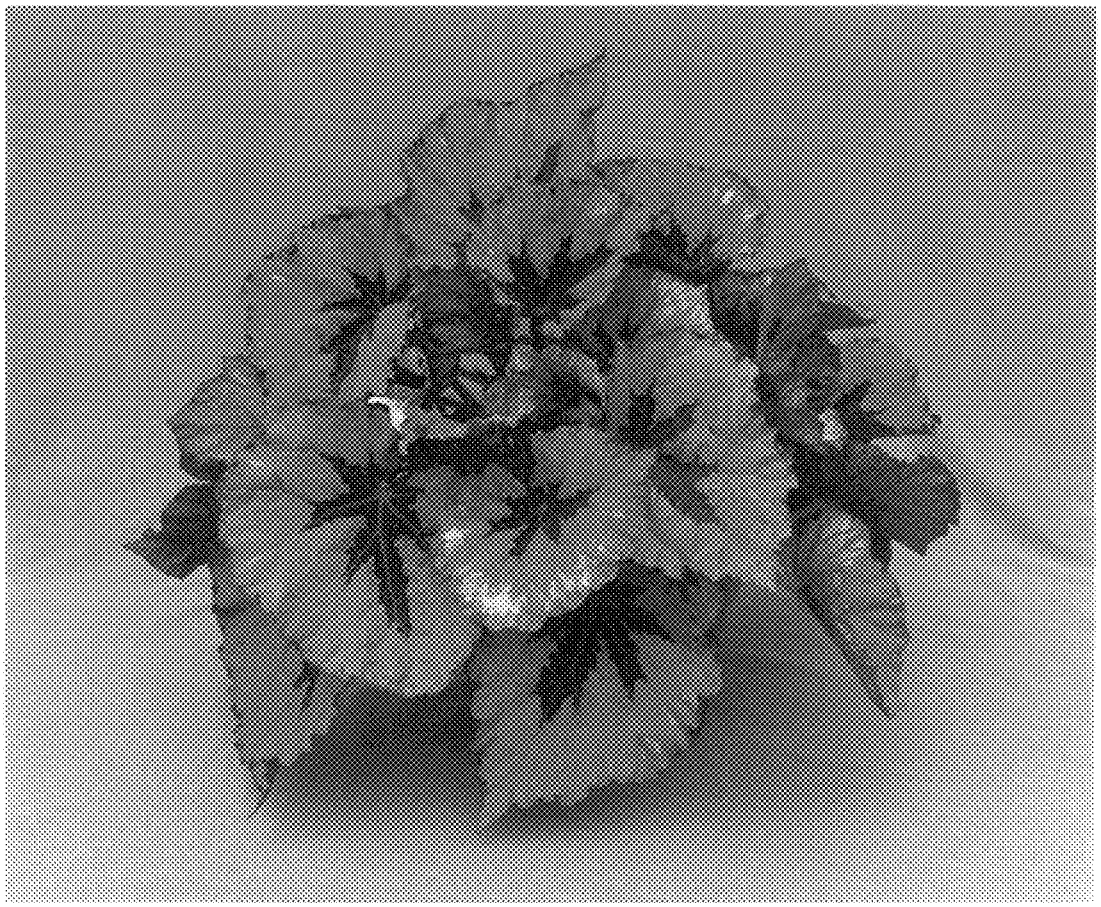

* * * * *